United States Patent [19]

Mori

[11] Patent Number: 4,974,922

[45] Date of Patent: Dec. 4, 1990

[54] LIGHT BATH

[76] Inventor: Kei Mori, 3-16-3-501, Kaminoge, Setagaya-ku, Tokyo, Japan

[21] Appl. No.: 394,595

[22] Filed: Aug. 16, 1989

[30] Foreign Application Priority Data

Nov. 21, 1988 [JP] Japan .............................. 63-294089

[51] Int. Cl.$^5$ .............................................. G02B 6/14
[52] U.S. Cl. .................................. 350/96.10; 128/372
[58] Field of Search ..................... 350/96.10; 128/362, 128/365-375

[56] References Cited

U.S. PATENT DOCUMENTS

| | | | |
|---|---|---|---|
| 4,100,415 | 7/1978 | Blaisdell et al. ................ | 128/371 X |
| 4,469,102 | 9/1984 | Fish .................................. | 128/371 X |
| 4,901,724 | 2/1990 | Mori ................................. | 128/372 |

Primary Examiner—John D. Lee
Assistant Examiner—Phan T. Heartney
Attorney, Agent, or Firm—Jordan and Hamburg

[57] ABSTRACT

A hexagonal-shaped chamber for taking a light bath has inner reflecting mirror surfaces and a plurality of light guides for radiating visible light rays into the chamber. One of the six side walls of the chamber is constructed as a door to be opened and closed. Some of the light guides are connected at their light-emitting ends to the other walls of the chamber at different levels so as to emit the light rays toward the inner opposite reflecting surfaces of the chamber. The remaining light guides are connected at their light-emitting ends to the top surface of the chamber so as to emit the light rays from their ends towards the inner bottom surface of the chamber.

6 Claims, 4 Drawing Sheets

LIGHT BATH

BACKGROUND OF THE INVENTION

The present invention relates to a light bath and more particularly to one capable of effectively applying visible light rays to all of the skin's surface to energize a person's skin as well as the internal organs.

In recent years, a large number of persons suffer from incurable diseases such as gout, neuralgia and rheumatism or pain from injuries, bone fractures and from other ill-defined diseases. Furthermore, no one can be free from their skin's aging which progresses gradually from a comparatively young age. On the other hand, the present applicant has previously proposed focusing solar rays or artificial light rays by using lenses or the like, to guide them into a fiber optic cable and to transmit them to any place where the light is needed for illumination or for other purposes as for example, to cultivate plants, chlorella, fish or the like. As a result of the applicant's research, it has been found that the visible light not containing ultraviolet and infrared rays is effective not only to promote health and to prevent one's skin from showing signs of aging but also to noticeably aid in healing gout, neuralgia, bedsores, rheumatism, burn, skin diseases, bone fracture, and so on and in relieving pain from such diseases. In order to relieve pain from such diseases it is usually necessary to irradiate the patient's diseased portion with visible light. However, in some instances, it has also been proven that irradiation with weak visible light rays may bring the same results in relieving the pain if the radiation time is prolonged. In practice, local radiation with weak light rays has been applied as therapy for various kinds of diseases. It is well known that sunbathing may promote the health of persons but sunlight includes ultraviolet rays which may exert an adverse effect on the skin. Therefore, sunbathing is prohibited to one who is in poor health. The accumulation of ultraviolet rays on people's skin may contribute to cancer while the accumulation of infrared rays may cause the skin to burn. Consequently, overexposure to light containing ultraviolet and infrared rays must be avoided.

In view of the foregoing explanation, the applicant has previously proposed a light bath that is safe by radiating light that contains no harmful ultraviolet and infrared rays. The light bath proposed by the applicant has the interior covered with mirrors and a light guide for supplying visible light rays into the light bath. Visible light rays emitted from the light guides are reflected on the inner surface of the light bath and thereby are evenly spread in the internal space of the light bath. Light-emitting points may be evenly arranged in the light bath. However, it may also be possible to arrange the light-emitting points in such a way as to supply stronger light rays to a certain place as for instance, a person's shoulders or to radiate light rays from fewer light emitting points and to further diffuse the light rays by reflecting them onto the inner wall of the light bath. A person enters into the light bath and expose his naked body to the light rays radiated therein as mentioned above. Accordingly, the light bath is provided with an access door that is easily opened. The light bath is also equipped with a cloth container fixed thereon for storing clothes that a person has taken off after having entered the bath. Furthermore, the upper cover member is made of a transparent material to allow the occupant to see outside and it can be opened from the inside to get to the outside for putting clothes into the cloth basket. The light bath allows the occupant to use therein such communication means as a wireless telephone, a push-button switch or others. When the light bath is equipped with a transparent foot plate for irradiating the light rays from the bottom up, the soles of the occupant's feet can be exposed to the light thereby promoting health by improving blood circulation. fiber optic cable for receiving sunlight or artificial light (xenon) at its input end from a solar ray collecting device and for transmitting the light therethrough. The light rays to be transmitted through said fiber optic cable are ones that correspond to the visible spectrum light (white light) obtainable in various ways as previously proposed by the present applicant.

When the light bath is used, a socket for the light-receiving end of the light guide is coupled with a socket for the light-emitting end of the fiber optic cable. At this time the light rays transmitted through the fiber optic cable are introduced into the light guide through the sockets coupled with each other and then they are radiated into the light bath and reflected on the inner walls of the light bath to be evenly applied to the entire surface of a person's body. The inside temperature of the light bath can be set at any desired level by introducing air previously heated or cooled to the desired temperature into the light bath with the use of an air hose which, at the time of light bathing, is connected to an air inlet provided at the upper portion of the light bath. The air introduced into the bath is then drawn out from the bath through an air outlet provided at a lower portion of the light bath. The above-mentioned light bath is constructed so that a person takes a light bath in a standing position. However, it is also possible to provide a light bath wherein a person may sit down or lie down by modifying the shape of the light bath as for example, a light bath with a reduced height or a horizontal type installed with a chair or a bed therein. When a chair or a bed made of a transparent material is installed in the modified light bath, a more effective light bath can be taken.

SUMMARY OF THE INVENTION

It is an object of the present invention to provide a light bath which, when compared with the light bath previously proposed by the present applicant, is improved in that a person can easily see the light rays fall on his body and can get a feeling of spaciousness inside the chamber.

DESCRIPTION OF THE PREFERRED EMBODIMENTS

Figure 1:
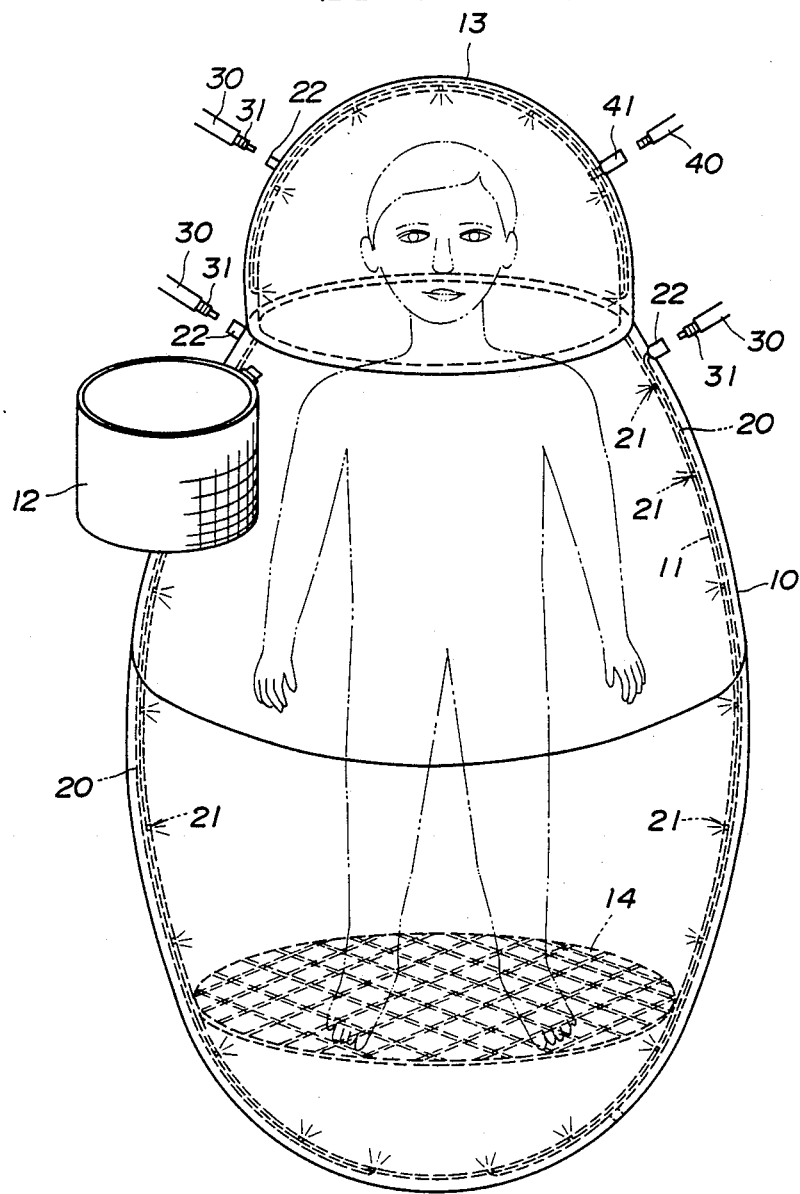
FIG. 1 is a view for explaining an embodiment of a light bath previously proposed by the present applicant.

FIG. 1 is a perspective view for explaining an embodiment of a light radiation device for use in medical treatment which was previously proposed by the present applicant. In FIG. 1, numeral 10 designates a light bath having the interior covered with mirrors 11 and numeral 20 designates a light guide for supplying visible light rays into said light bath 10. Visible light rays emitted from the light guides 20 are reflected on the inner surface 11 of the light bath 10 and thereby evenly spread in the internal space of the light bath 10. Light emitting points may be evenly arranged in the light bath 10 as shown in FIG. 1. However, it may also be possible to arrange the light emitting points in such a way as to supply stronger light rays to a certain place as for instance, a person's shoulders or to radiate light rays from fewer light emitting points and to further diffuse the light rays by reflecting them onto the inner wall of the light bath 10. As shown in FIG. 1, a person enters into the light bath and exposes his naked body to the light rays radiated therein as mentioned above. Accordingly, the light bath 10 is provided with an access door that is easily opened. The light bath is also equipped with a cloth container fixed thereon for storing clothes that a person has taken off after having entered the bath. Furthermore, an upper covering member 13 is made of a transparent material to assure an outward view from the inside of the light bath 10 which can be opened from the inside of the light bath 10 to get to the outside and to put clothes into the cloth basket 12. The light bath 10 allows the occupant to use therein such communication means as a wireless telephone, a push-button switch or others. When the light bath is equipped with a transparent foot plate 14 for irradiating the light rays from the bottom up, the soles of the occupant's feet can be exposed to the light thereby promoting health by improving blood circulation. Numeral 30 designates a fiber optic cable for receiving sunlight or artificial light (xenon) at its input end, not shown in FIG. 1, from a solar or artificial light ray collecting device and for transmitting the light therethrough. The light rays to be transmitted through said fiber optic cable 30 are ones that correspond to the visible spectrum light obtainable in various ways as was previously proposed by the present applicant.

When the light bath is used, a socket 22 for the light-receiving end of the light guide 20 is coupled with a socket 31 for the light-emitting end of the fiber optic cable 30. At this time the light rays transmitted through the fiber optic cable 30 are introduced into the light guide 20 through the sockets coupled with each other and then they are radiated into the light bath 10 and reflected on the inner walls of the light bath to be evenly applied to the entire surface of a person's body. The inside temperature of the light bath 10 can be controlled at a desired level by introducing air previously heated or cooled to a desired temperature into the light bath with the use of an air hose 40 which, at the time of light bathing, is connected to an air inlet 41 provided at the upper portion of the light bath 10. The air introduced into the bath is then drawn out from the bath through an air outlet provided at a lower portion of the light bath. The above-mentioned light bath is constructed so that a person takes a light bath in a standing position. However, it is also possible to provide a light bath wherein a person may sit down or lie down by modifying the shape of the light bath as for example, a light bath with a reduced height or a horizontal type installed with a chair or a bed therein. When a chair or a bed made of transparent material is installed in the modified light bath, a more effective light bath can be taken.

Figure 2:
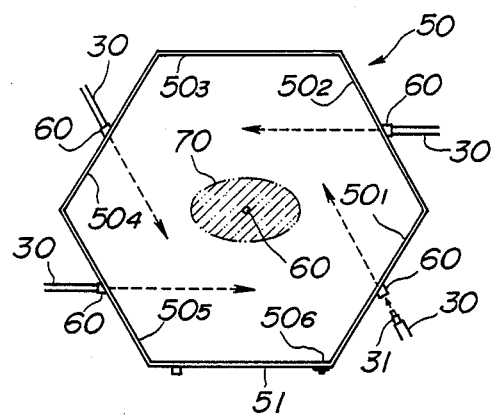
FIG. 2 is a plane view for explaining an embodiment of a light bath according to the present invention.
Figure 3:
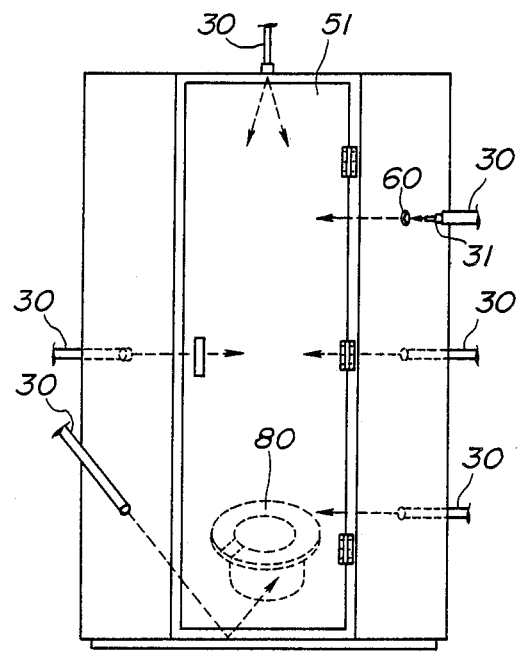
FIG. 3 is a front view of the light bath according to the present invention.

FIGS. 2 and 3 are views for explaining an embodiment of a light bath according to the present invention. FIG. 2 is a plane view and FIG. 3 is a front view of the light bath. In FIGS. 2 and 3, plates $50_1$–$50_6$, each of which has a reflecting (mirror finished) inner surface, are integrally connected with each other to form a hexagonal chamber 50 having ports 60 for connecting the sockets 31 of the light-emitting ends of the fiber optic cables 30. Light rays transmitted through the fiber optic cables 30 are thus introduced into the chamber 50 and reflected by the reflecting plates $50_1$–$50_6$ and then fall on the subject 70 to be exposed to the light rays in the chamber 50.

Since the light bath, according to the present invention, is intended for persons, its chamber 50 is designed to have one door 51 to be freely opened and shut and to have on the other side of the ports 60 connections for the light-emitting ends of the fiber optic cables. In practice, the light-emitting ends of the fiber optic cables can be connected at different levels and at different angles to each of the hexagonal chamber's sides except the door side, so that all of a person's body, even in a standing position, may be exposed to an even amount of light rays. Furthermore, inside the hexagonal chamber a chair 80 made of a transparent material is installed thereby allowing a person to sit therein during a light bath. In this case, it is possible to adjust any one of the light radiating points at the chamber's sides to direct the light rays therefrom towards the floor's surface to be reflected towards a center portion on the bottom of the transparent chair through which the reflected light rays can be applied to the buttocks and to the portion of the body between the legs of the person sitting in the chair. Furthermore, it is also possible to evenly radiate the head and shoulders by introducing light rays into the light bath through a light radiating point provided at the top of the chamber.

As is apparent from the foregoing description, since the light bath, according to the present invention, has a hexagonal shape' with mirror finished inside walls to reflect light rays, a person who is enjoying a light bath can clearly see the light rays fall on his body and can thereby receive the light rays more effectively.

If the light bath has a cylindrical body, the image formed on its inside walls is distorted into a large size. If the light bath has a pentagonal body, a double image is formed on each of its inside walls. Furthermore, if the light bath has an octagonal body, it becomes impossible to see the whole image of the person's body on each of its inside walls because of the insufficient width of each wall.

The light bath according to the present invention is capable of radiating light rays therein from all sides (excepting the door side) of its hexagonal body at different heights and in different directions as well as from the top and bottom. This means that inside it a person can enjoy more effectively a complete light bath by receiving the light rays evenly all over the body.

Figure 4:
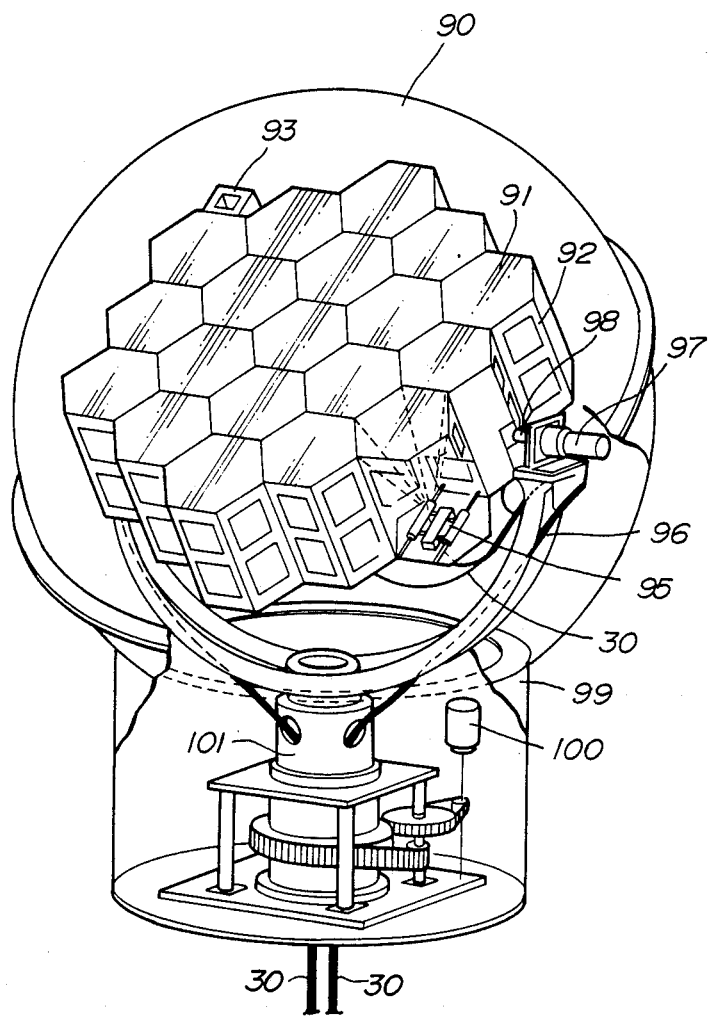
FIG. 4 is a view illustrating a solar ray collecting device which serves as an example of a system for introducing light rays into a fiber optic cable.

FIG. 4 is a construction view for illustrating, by way of example, a solar ray collecting device for guiding the sunlight into the aforesaid fiber optic cable. In FIG. 4, numeral 90 is a transparent capsule, 91 is a Fresnel lens, 92 is a lens holder, 93 is a solar position sensor, 30 is an optical fiber or a fiber optic cable consisting of a large number of optical fibers having light-receiving end surfaces set on the focal plane of the Fresnel lens system, 95 is a holder of the optical fibers or of the fiber optic cable, 96 is an arm, 97 is a pulse motor, 98 is a horizontal rotary shaft to be driven by the pulse motor 97, 99 is a base for supporting the protective capsule 90, 100 is a pulse motor and 101 is a vertical rotary shaft to be driven by the pulse motor 100.

The direction of the sun is detected by means of the solar position sensor 93 and its detection signal controls the pulse motors 97 and 100 of the horizontal and vertical rotation shafts 97 and 100 respectively so as to always direct the solar position sensor toward the sun, and the sunlight focused by the lens 91 is guided into the fiber optic cable 30 through its end-surface set at the focal point of the lens. All of the light guides 30, separately placed at each lens, are bundled together in a fiber optic cable, the free end of which is led to any place where light radiation is needed for the afore-mentioned purposes.

Figure 5:
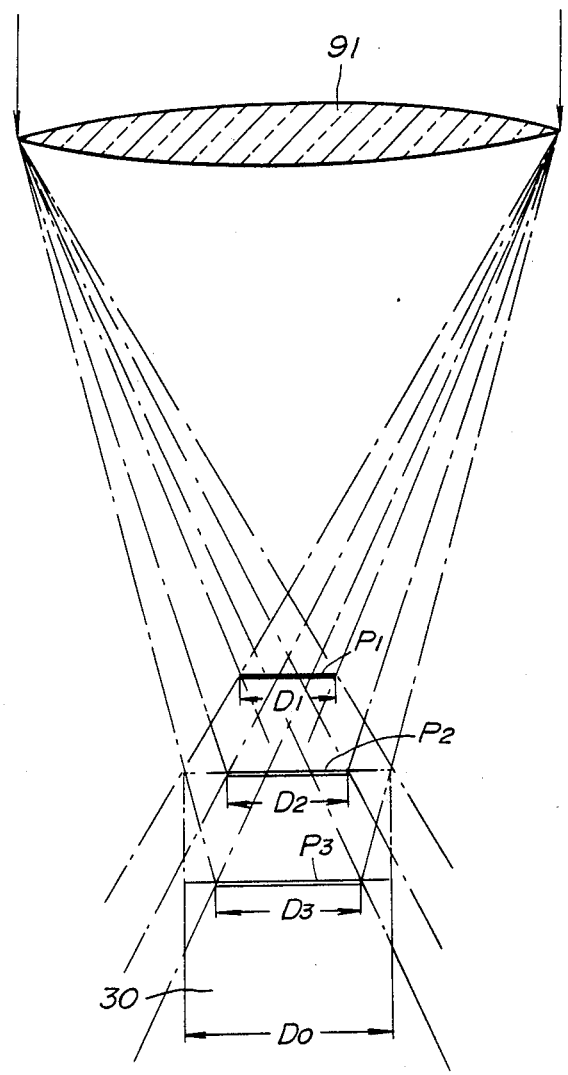
FIG. 5 is a view for explaining a practical method for introducing light rays into a fiber optic cable.

FIG. 5 is a view for explaining how to guide the solar rays collected by the above-mentioned lens 31 into the light guides. In FIG. 5, 91 is a Fresnel lens or the like and 30 is a light guide which receives the sunlight focused by the lens 91 and which transmits the same to any desired place. In case of focusing the sunlight through the lens system, the solar image has a central portion consisting of almost white light and a circumferential portion containing therein a large amount of the light components having wave-lengths corresponding to the focal point of the lens system. Namely, in the case of focusing sunlight through the lens system, the focal point and the size of the solar image will vary in accordance with the component wave-lengths of the light. For instance, the blue color light having a short wave-length makes a solar image of diameter D1 at position P1. Furthermore, the green color light makes a solar image of diameter D2 at position P2 and the red color light makes a solar image of diameter D3 at position P3. Consequently, as shown in FIG. 5, when the light-receiving end-surfaces of the light guides are set at position Pl, it is possible to collect the sunlight containing plenty of the blue color components at the circumferential portion thereof. When the light-receiving end-surfaces of the light guides are set at position P2, it is possible to collect the sunlight containing plenty of the green color components at the circumferential portion thereof. When the light-receiving end-surfaces of the light guides are set at position P3 it is possible to collect the sunlight containing plenty of red color components at the circumferential portion thereof. In each case, the diameter of the light guide 30 can be selected in accordance with the light components to be collected. For instance, the required diameters of fiber optic cables are D1, D2 and D3, respectively, depending on the colors of the light rays to be stressed, i.e. the blue, green and red colors. In such a way, the required amount of the light guides can be saved and thereby the sunlight containing therein plenty of desired color components can be collected most effectively.

And further, as shown in FIG. 5, if the diameter of the light-receiving end-surface of the light guide is enlarged to D0, it may be possible to collect visible light containing therein all of its wavelength components. The light guides 30 may be pre-set at the focal point of the lens system in the manufacturing process or they may be left in an adjustable condition in the axial direction of the lens system to allow the user to adjust and fix said light guides depending upon the desired color of the light to be obtained. By selecting the wave-length of the light components to be introduced into the fiber optic cable, it becomes possible to use the light radiating system more effectively for various purposes. The above-mentioned example relates to the device for introducing the solar rays into the fiber optic cable. However, it is also possible to introduce artificial light into the fiber optic cable.

I claim:

1. A light ray radiation device for use in treatment of a person's body or a person's body part comprising a hollow enclosure means having a longitudinal axis and six elongated flat side plates generally parallel to said axis, said side plates being arranged as a hexagonal polygon to thereby define a hollow interor of said enclosure means, said side plates having interior mirror surfaces which reflect light rays, optical conductor means for conducting the visible light ray component of solar rays from which ultraviolet and infrared rays have been excluded, connecting means mounted in and extending through one of said side plates, said conductor means having an end portion which is mounted in said connecting means such that said visible light ray component of solar rays conducted by said conductor means is emitted from said conductor means into the interior of said hollow enclosure means, said end portion of said conductor means having a longitudinal axis which is disposed at an acute angle relative to said one side plate such that said emitted light ray component is reflected by said mirror surfaces of said side plates to provide for radiation of a person or a person's body part disposed in said hollow enclosure means.

2. A light ray radiation device according to claim 1, wherein said hollow enclosure means has a bottom floor, second optical conductor means for conducting the visible light ray component of solar rays from which ultraviolet rays and infrared rays have been excluded, and a second connecting means mounted in and extending through another of said side plates, said second conductor means having an end portion which is mounted in said second connecting means such that said visible light ray component of solar rays conducted by said second conductor means is emitted from said second conductor means into the interior of said hollow enclosure means, said end portion of said second conductor means having a longitudinal axis which is disposed at an acute angle relative to said bottom floor such that the visible light ray component emitted from said end portion of said second conductor means is directed generally downwardly to said floor and is reflected upwardly from said floor into the interior of said hollow enclosure means onto said person's body or said person's body part disposed in said hollow enclosure means.

3. A light ray radiation device according to claim 1, further comprising a second optical conductor means for conducting the visible light ray component of solar rays from which ultraviolet rays and infrared rays have been excluded, and second connecting means mounted in and extending through another of said side plates, said second conductor means having an end portion which is mounted in said second connecting means such that said visible light ray component of solar rays conducted by said second conductor means is emitted from said second conductor means into the interior of said hollow enclosure means, said end portion of said second conductor means having a longitudinal axis which is disposed at an acute angle relative to said another side plate such that said emitted light ray component is reflected by said mirrored surface of said side plates so as to provide for radiation of said person's body or said person's body part disposed in said hollow enclosure means.

4. A light ray radiation device for use in medical treatment of a person's body or a person's body part comprising a hollow enclosure means having a longitudinal axis and a plurality of elongated flat side plates generally parallel to said axis, said hollow enclosure means also having a bottom floor, said side plates being arranged as a polygon to thereby define a hollow interior of said enclosure means, said side plates having interior mirror surfaces which reflect light rays, first optical conductor means for conducting the visible light ray component of solar rays from which ultraviolet and infrared rays have been excluded, first connecting means mounted in and extending through one of said side plates, said first conductor means having an end portion which is mounted in said first connecting means such that said visible light ray component of solar rays conducted by said first conductor means is emitted from said first conductor means into the interior of said hollow enclosure means, said end portion of said first conductor means having a longitudinal axis which is disposed at an acute angle relative to said one side plate such that said emitted light ray component is reflected by said mirror surfaces of said side plates to provide for radiation of a person or person's body part disposed in said hollow enclosure means, second optical conductor means for conducting the visible light ray component of solar rays from which ultraviolet rays and infrared rays have been excluded, second connecting means mounted in and extending through another of said side plates, said second conductor means having an end portion which is mounted in said second connecting means such that said visible light ray component of solar rays conducted by said second conductor means is emitted from aid second conductor means into the interior of said hollow enclosure means, said end portion of said second conductor means having a longitudinal axis which is disposed at an acute angle relative to said another side plate such that said emitted light ray component is reflected by said mirrored surface of said side plates so as to provide for radiation of said person's body or said person's body part disposed in said hollow enclosure means, third optical conductor means for conducting the visible light rays component of solar rays from which ultraviolet rays and infrared rays have ben excluded, and third connecting means mounted in and extending through another of said side plates, said third conductor means having an end portion which is mounted in said third connecting means such that said visible light ray component of solar rays conductor by said third conductor means is emitted from said third conductor means into the interior of said hollow enclosure means, said end portion of said third conductor means having a longitudinal axis which is disposed at an acute angle relative to said bottom floor such that the visible light ray component emitted from said end portion of said third conductor means is directed generally downwardly to said floor and is reflected upwardly from said floor into the interior of said hollow enclosure means onto aid person's body or said person's body part disposed in said hollow enclosure means.

5. A light ray radiation device according to claim 4, further comprising a chair means in said hollow enclosure on said floor, said chair means being made of transparent material such that the light rays reflected generally upwardly from said floor pass through said transparent material of said chair onto a person's body part disposed on said chair.

6. A light ray radiation device according to claim 4, wherein said hollow enclosure means comprises a top wall, fourth optical conductor means for conducting the visible light ray component of solar rays from which ultraviolet and infrared rays have been excluded, fourth connecting means mounted in and extending through said top wall, said fourth conductor means having an end portion which is mounted in said fourth connecting means such that said visible light ray component of solar rays conductor by said fourth conductor means is emitted from said fourth conductor mans into the interior of said hollow enclosure means such that said emitted light ray component provides for radiation of a person or a person's body part disposed in said hollow enclosure means.

* * * * *